(12) United States Patent  
Akkus et al.

(10) Patent No.: US 10,024,798 B2  
(45) Date of Patent: Jul. 17, 2018

(54) MULTIFOCAL HYPERSPECTRAL RAMAN SYSTEM AND METHODS FOR IMAGING OF MATERIALS

(71) Applicant: CASE WESTERN RESERVE UNIVERSITY, Cleveland, OH (US)

(72) Inventors: Ozan Akkus, Brooklyn, OH (US); Shan Yang, Cleveland Heights, OH (US)

(73) Assignee: CASE WESTERN RESERVE UNIVERSITY, Cleveland, OH (US)

(*) Notice: Subject to any disclaimer, the term of this patent is extended or adjusted under 35 U.S.C. 154(b) by 586 days.

(21) Appl. No.: 14/600,603

(22) Filed: Jan. 20, 2015

(65) Prior Publication Data

US 2015/0204789 A1  Jul. 23, 2015

Related U.S. Application Data

(60) Provisional application No. 61/929,352, filed on Jan. 20, 2014.

(51) Int. Cl.
| | |
|---|---|
| G01N 21/65 | (2006.01) |
| G01J 3/28 | (2006.01) |
| G01J 3/44 | (2006.01) |

(52) U.S. Cl.
CPC ............ G01N 21/65 (2013.01); G01J 3/2823 (2013.01); G01J 3/4412 (2013.01); *G01N 2201/06113* (2013.01)

(58) Field of Classification Search
CPC ....................................................... G01N 21/65
See application file for complete search history.

(56) References Cited

U.S. PATENT DOCUMENTS

| | | | |
|---|---|---|---|
| 7,057,721 B2 | 6/2006 | Gardner, Jr. et al. | |
| 8,537,260 B2 | 9/2013 | Daigle | |
| 2007/0166045 A1* | 7/2007 | Wang .................. | G02B 27/283 398/152 |
| 2008/0192246 A1* | 8/2008 | Neiss ....................... | G01J 3/02 356/301 |

* cited by examiner

*Primary Examiner* — Manuel A Rivera Vargas
(74) *Attorney, Agent, or Firm* — Hudak, Shunk & Farine Co. LPA

(57) ABSTRACT

A hyperspectral Raman imaging system having the ability to focus on excitation laser beam over a relatively wide field of view due to the use of a lens array, in particular a microlens array. Hyperspectral selection is provided in one embodiment through the use of dual-axis controlled dielectric filtration. Methods for analyzing materials with the system are disclosed. The device or system can be used in generally any application where investigation of materials is required.

15 Claims, 4 Drawing Sheets

MULTIFOCAL HYPERSPECTRAL RAMAN SYSTEM AND METHODS FOR IMAGING OF MATERIALS

FIELD OF THE INVENTION

The present invention relates to a multifocal hyperspectral Raman imaging system having the ability to focus on excitation laser beam over a relatively wide field of view due to the use of a lens array, in particular a microlens array. Hyperspectral selection is provided in one embodiment through the use of dual-axis controlled dielectric filtration. Methods for analyzing materials with the system are disclosed. The device or system can be used in generally any application where investigation of materials is required.

BACKGROUND OF THE INVENTION

Raman spectroscopy or imaging is a useful and powerful spectroscopic tool for chemical analysis of materials. Raman imaging relies on scattering of light, usually from a laser, preferably a monochromatic laser in the visible, near infrared, or near ultraviolet range. When the incident light utilized is monochromatic, the light reflected from the irritated area differs in wavelength from that of the light source, with the wavelength shift being utilized to determine the molecular composition of the material.

Raman spectroscopy is a fundamental tool used in materials science, biology, ceramics, pharmaceuticals, semi-conductors, energy, polymers, medicine, chemistry and physics. Raman spectroscopy can be utilized to analyze both dry (solid), gaseous and aqueous materials and requires little or no sample preparation. It provides information on the type of chemical bonds present in the analyte over a sample volume illuminated by a laser light. Included in the Raman spectrum is the information on the amount of chemical species, the macroscopic (crystallinity) and nanoscale morphology (molecular alignment) of the compound as well as its purity.

Raman spectroscopy can generate chemical images by collecting multiple observations (point by point, or line-scan mapping) over the sample space. It can take hours, sometimes a significant fraction of a day to generate such images. Therefore, Raman mapping is inapplicable for the analysis of dynamic systems or real-time imaging using available commercial systems. As an alternative to rastering the sample space, others have resorted to 2D-CCDs to acquire the Raman image in the wavenumber of interest (so called global Raman imaging). This has met with partial success; however, such systems are costly and they provide information over a limited field of view (less than 0.25 mm). Accordingly, existing global Raman imaging systems are cost-prohibitive, and they may still need rastering for larger field of views.

Users of Raman imaging are researchers in the academia, pharmaceutical industry, semiconductor industry, polymers, ceramics, forensic labs and art museums. To illustrate an application: active pharmaceutical ingredient (API) of drug tablets cannot be investigated expeditiously enough by Raman at the production line. Or, real-time monitoring of carbon nanotubes during synthesis is not feasible with Raman. Or, the build-up and loss of charged species in a lithium ion battery cannot be visualized over the full field of view. These are few examples where users have unmet needs.

In global Raman imaging, a tunable band-filter (dielectric or tunable liquid crystal filter) that passes only the wavenumber range of interest from the analyte allows the collection of Raman intensity distribution over each pixel of the 2D-CCD array over the entire field of view. In applications where the analyte information is obtainable from a single peak, the image can be acquired in a single acquisition sequence. In present versions of global Raman imaging, the excitation is applied to the sample via a single lens. This effectively illuminates less than 10% of the field of view at the center which in turn means that data are not collected from more than 90% percent of the sample space, see FIG. 1A for example. While the 2D CCD can gather information all around, limitation of the excitation to the central region limits data collection to the center.

In summary, various Raman imaging systems can have drawbacks including one or more of limited fields of view, relatively high cost to obtain, and long signal acquisition times. These limitations hinder the expansion of Raman imaging to real-time and/or high volume applications.

SUMMARY OF THE INVENTION

In view of the above, a problem to be solved by the present invention was to develop a Raman imaging system having a relatively large field of view. Another problem to be solved was to reduce the signal acquisition time of a Raman imaging system. Yet another problem to be solved was to reduce the cost of ownership of a Raman imaging system such that various government, academic, and industrial entities could afford the cost of ownership for such a system.

These and other problems that will become apparent by reading the description herein are solved by the hyperspectral Raman imaging system disclosed.

In view of the above, it is an object of the present invention to provide a Raman imaging system with the ability to realize multiple focus points of an excitation laser beam over a field of view, in particular a full field of view utilizing an array comprising a plurality of lenses and, in particular, one or more microlens arrays.

Yet a further object of the present invention is to provide a Raman imaging system including a novel dual-axis kinematically controlled filtration in order to extract desired spectral information at each pixel which is imaged.

Still another object of the present invention is to provide a Raman imaging system that includes a combination of multiple focusing of the excitation light source or laser beam over a desired field of view via a lens array comprising a plurality of lenses and also hyperspectral selection using dual-axis control dielectric filtration.

A further object of the present invention is to provide a Raman imaging system having one or more of a relatively wide field of view, relatively low cost of ownership and shorter image acquisition times. Images which are collected in hours, minutes or seconds with standard systems can be imaged with the proposed system in minutes, seconds, or milliseconds, respectively.

Yet another object of the present invention is to enable real-time Raman analysis of dynamic processes. The improvement is meaningful for static systems as well, by expediting data collection, for example from days to about an hour for a set of samples in one embodiment, whereby more samples can be processed, decreasing the time constant for discovery by orders of magnitude and enabling the analysis of a meaningful number of samples. This would increase acceptance of the proposed devices for quality control applications, such as pharmaceutical, carbon nanotube, and semiconductor industries, where subsets of samples can be expeditiously analyzed in the production line.

Accordingly, in one aspect, a Raman imaging system is disclosed, comprising an excitation source providing a beam; and a lens array located downstream from the excitation source in a beam path and including a plurality of lenses that split the beam into a plurality of beams, wherein the plurality of beams are adapted to be routed onto a sample, wherein a Raman signal received from the sample is routed to a charge-coupled device located downstream from the lens array.

Accordingly, in another aspect, a Raman imaging system is disclosed, comprising an excitation source providing a beam; and a dual-axis controlled dielectric filter located downstream from the excitation source in a beam path that provides for hyperspectral selection, and a charge-coupled device located downstream from the lens array.

Accordingly, in another aspect, a method for non-flat surface correction of Raman image is disclosed, comprising the steps of obtaining a Raman image; obtaining a reference image; dividing the Raman image by the reference image to normalize for relative variations and spacial intensity, which can be expressed as $$I_{corr} = \frac{I_{adjusted\ raw}}{I_{ref}},$$

where $I_{adjusted\ raw}$ is an intensity matrix of the raw image which can be adjusted by one or more of smoothing, filtering and subjecting to another form of numerical processing, $I_{ref}$ is an intensity matrix of the reference image, and $I_{corr}$ is an intensity variance corrected final image.

BRIEF DESCRIPTION OF THE DRAWINGS

The invention will be better understood and other features and advantages will become apparent by reading the detailed description of the invention, taken together with the drawings, wherein.

DETAILED DESCRIPTION OF THE INVENTION

Figure 1:
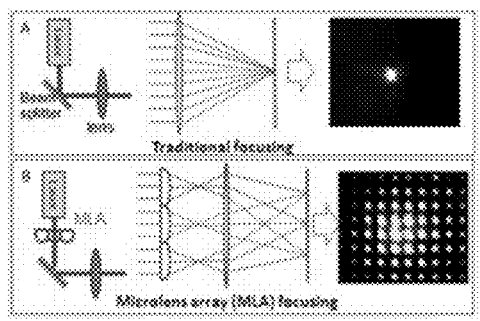
FIG. 1 is a schematic illustrating A) one example of classical excitation with a single focal point at the center and B) that the introduction of a plurality of lenses, in particular in the form of a microlens array (MLA) in the excitation path of a Raman imaging system that splits a beam received from the excitation source and produces a plurality of excitation spots that are spread over an area larger than the area of the beam of the excitation source, with the larger area preferably covering the full field of view.
Figure 3:
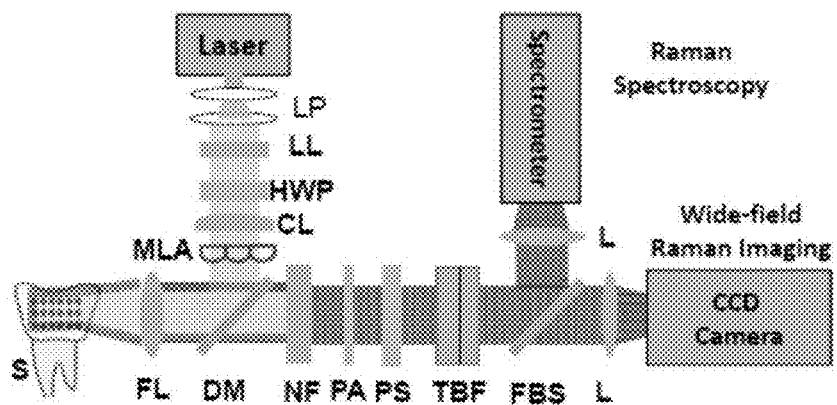
FIG. 3 is a schematic view of one embodiment of the components and layout of a wide-field Raman imaging system of the present invention utilizing a lens array, wherein MLA is a microlens array, TBF is a tunable band-pass filter, DM is a dichroic mirror, NF is a notch filter, LL is a laser line filter, FL is a focusing lens, L is a lens, CL is a cylindrical lens, LP is a telescope lens pair, FBS is a flip beam splitter, P is a linear polarizer, HWP is a half-wave plate, PA is a polarization analyzer, and PS is a polarization scrambler.
Figure 7:
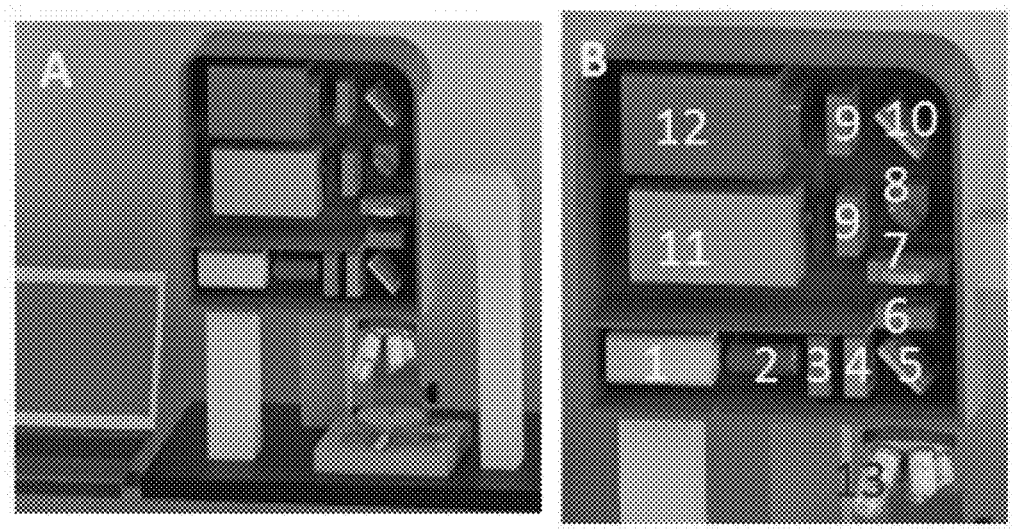
FIG. 7 illustrates another embodiment of a multi-lens array-containing Raman imaging system of the invention including A) an overview and B) the following components 1: Laser, 2: Lens pair or beam expander, 3: laser filter, 4: microlens array, 5: dichroic mirror, 6: edge filter, 7: tunable kinematic band-pass filter, 8: flip mirror, 9: lens, 10: mirror, 11: spectrometer, 12: 2D-CCD camera, 13: objectives/lenses.

As indicated herein, one embodiment of the present invention discloses a multifocal hyperspectral Raman imaging system. As illustrated in FIGS. 1, 3 and 7, in one embodiment the excitation scheme employs a lens array including a plurality of lenses, preferably a microlens array, to spread the excitation spots over a desired, large or full field of view. Thus, the plurality of lenses, e.g. microlens array, in a beam path increase an area (cross-section that is perpendicular to the beam path) of a beam generated by an excitation source from an initial area to a larger area, wherein the larger area is generally at least 25%, desirably at least 50%, and preferably at least 90% larger than the area of the beam incident on a first lens of the plurality of lenses or on the microlens array. In one embodiment, direct imaging of areas, for example up to 5×5 mm, an order of magnitude of better coverage than known existing systems is possible with high power lasers. Discretization of excitation reduces the risk of damage to the sample; while enabling the utilization of a high power laser.

A series of dielectric band-pass filters can be used to isolate the wavenumbers of interest on the Raman signal path. It is optionally possible to scan a wavenumber range using the computer controlled kinematic wavenumber filters, enabling the acquisition of hyperspectral images, see FIGS. 2 and 7 for example.

Variations in illumination over the space continuum (due to distortions introduced by optical components and surface curvature of samples) can be corrected by reference images. Software can streamline the registration of the reference and Raman image sequences and process them to generate corrected images.
by reference images. Software can streamline the registration of the reference and Raman image sequences and process them to generate corrected images.

With respect to hardware, a suitable excitation source is chosen, preferably a monochromatic laser having a wavelength of from about 250 to about 1064 nm. In the examples set forth hereinbelow a 785 nm laser was utilized. A 532 nm wavelength can also be utilized in other embodiments which results in a reduced risk of damage to a sample. Lasers having a higher power, such as 1064 nanometers can also be utilized and are preferred in some embodiments in order to reduce background fluorescence. A negative cylindrical lens, for example f=−200 mm, can be used to defocalize the laser spot onto a rectangular profile on the sample. Other lenses can be used so that the field of view can be expanded.

A telescope lens pair is located downstream from the laser. Placed thereafter is a laser line filter and a cylindrical lens. After passing therethrough, the light encounters a dichroic mirror and subsequently is passed or routed through a focusing lens onto the sample. The scattered Raman signal from the sample is then routed through an edge filter, a tunable band-pass filter to a flip beam splitter which can be used to route the signal to the spectrometer and also be flipped off during the image acquisition so that a full Raman signal can be delivered to a charge-coupled device or CCD camera. As illustrated in FIG. 3, a lens array including a plurality of lenses, such as a microlens array is placed in the excitation path to spread the excitation spots over a full or desired field of view.

In one embodiment, a microlens array, such as available from Thorlabs as model MLA150-7AR-M or SUSS MicroOptics of Switzerland as model number 18-00232, can be utilized. The microlens array discretizes the laser power to an array of spots which in turn spreads the laser power over the desired or full field of view. As mentioned above, this results in reduced risk of damage to the sample while enabling the utilization of high power laser.

The embodiment set forth in FIG. 3 also includes a linear polarizer, half-wave plate, notch filter, a polarization analyzer, a polarization scrambler and a tunable bandpass filter. Depending on the mode of data collection, such as Raman spectrometer, wide field at 2D CCD or polarized analysis, some of the optics can be removed or even other optics can be added, as known to those of ordinary skill in the art.

Figure 4:
FIG. 4 illustrates one embodiment of a kinematic dielectric wavenumber filtering system of another innovative aspect of the present invention that enables hyperspectral imaging, wherein in one embodiment a motorized wheel can accommodate 1 to 10 band-pass filters which can be switched controllably to cover different wavenumbers, wherein the azimuthal rotation enables wavelength tuning to cover a range near or around a given wavenumber.

As described hereinabove, in one embodiment the tunable bandpass filter provides this system with hyperspectral imaging. Hyperspectral imaging allows use of the Raman imaging system with a broad range of applications which cannot be met by a set number of wave numbers. The system includes a bandpass filter which allows a 4D imaging modality where two dimensions are the axes of the imaging plane. One dimension is associated with the wavenumber and the temporal acquisition is the fourth dimension. In this option, a given dielectric filter is rotated azimuthally, see FIG. 4, to cover a wavenumber range of ±250 cm$^{-1}$ about the central wavenumber of the dielectric filter. For instance, covering a range of 200-1200 cm$^{-1}$ requires two dielectric filters which are centered at 400 cm-1 and 950 cm$^{-1}$. The filter wheel programmed to engage the filter #1, rotate filter #1 azimuthally, engage the filter #2, rotate filter #2 azimuthally, to cover the said range. In this fashion, a range up to 2700 cm$^{-1}$ is covered.

A spectrometer is used after the dielectric filters on the signal collection path to enable the tuning of kinematic dielectric band-pass filter to the wavenumber of interest; and, to collect full wavenumber range Raman spectrum of the same region to validate the wide-field image. A flip beam splitter is used to switch between the spectrometer and the imaging camera. The splitter can be manually switched by a mechanical knob that is accessible from outside the housing in one embodiment. Alternative to the spectrometer, tuning and calibration of the kinematic band-pass filter can be accomplished by providing light sources at known wavelengths by using tungsten halogen lamp as a source and a set of bandpass filter set at various wavelengths.

The following results illustrate that multilens arrays can be used to excite the desired or full field of view as a series of discrete points and adjustability of the field of view coverage.

Figure 5:
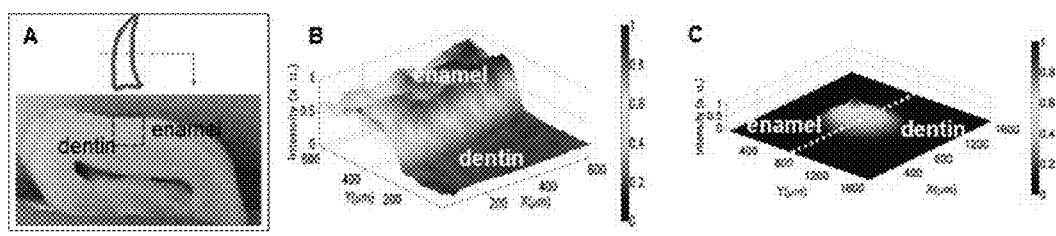
FIG. 5 illustrates A) tooth specimen was sectioned transversely to expose enamel-dentin junction at which the mineral content increases spontaneously, B) Raman point map of mineral variation at dentin (blue, low mineralization) and enamel (red, high mineralization) junction that lasted for 2 hours, C) single spot global Raman image of similar region that lasted for 1 minute, wherein however, meaningful information was limited to the center of the field of view. Intensity plots are the vertical red dashed lines.

There is a stepwise increase in the mineral content at the junction of enamel (highly mineralized) and dentin (partially mineralized) regions of tooth. This predictable increase in mineral content is a good test case to assess performance of chemical imaging methods. The enamel dentin junction was exposed by cutting a section perpendicular to the longer axis of the tooth (FIG. 5A).

Hardware

Figure 2:
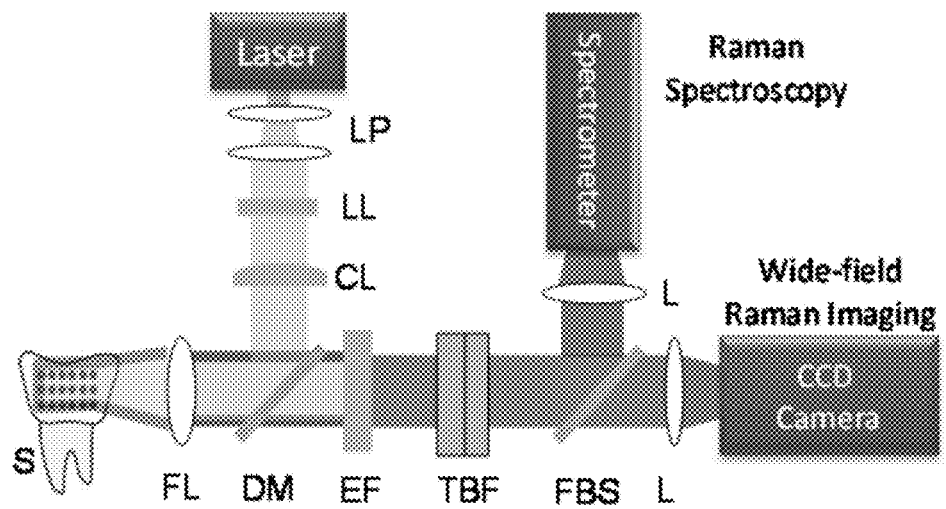
FIG. 2 is a schematic view of one embodiment of the components and layout of a wide-field Raman imaging system of the present invention utilizing dual-axis controlled dielectric filtration, wherein LP is a telescope lens pair, LL is a laser line filter, CL is a cylindrical lens, FL is a focusing lens, DM is a dichroic mirror, EF is an edge filter, TBF is a tunable band-pass filter wherein the filter can be rotated to scan a range of wavelength numbers, also enabling the acquisition of a continuous spectrum at each pixel (hyperspectral Raman analysis), FBS is a flip beam splitter and L is a lens.

The excitation source was a 785 nm laser (50 mW on sample) (FIG. 2). A negative cylindrical lens (f=−200 mm) was used to defocalize the laser spot into a rectangular profile on the sample. Other lenses were also used to demonstrate that the field of view can be expanded. An edge notch filter at 785 nm suppressed the residual excitation.

A dielectric filter was used to retain the wavenumber of interest corresponding to mineral Raman signal (at 960 cm$^{-1}$ originating from phosphate groups of mineral). The dielectric filter can be rotated to scan a range of wavenumbers, also enabling the acquisition of a continuous spectrum at each pixel (hyperspectral Raman analysis). For this particular application, acquisition at a fixed wavenumber is sufficient to get the information on mineral content. The global Raman image was captured by a near-infrared CCD camera (Ikon-M 934, loaned by Andor, USA). Signal integration time ranged from 60-120 seconds. The flip mirror was used to route the signal to the spectrometer which is used to confirm that the dielectric filter is rotated to an angle that provides the desired Raman wavenumber range. The mirror was flipped off during the image acquisition so that full Raman signal can be delivered to the CCD camera.

The regions observed by the wide-field system were also mapped by a Raman microscope (Xplora, 785 nm, Horiba Jobin Yvon) to confirm the observations of the global Raman imaging system. Images were point mapped at 40×40 points with 25 μm increment.

Data Analysis

The dark current noise due to deep cooling was acquired pre hoc and autocorrected for every image. Background fluorescence was photobleached until it was stabilized following which the image was acquired. A second image was captured at the base of the mineral peak at ~880 cm$^{-1}$ to correct for background fluorescence by subtracting the background intensity image from the image collected at 960 cm$^{-1}$ peak of mineral phosphate symmetric stretch band. Outlier points due to cosmic radiation were removed from the background corrected image.

Results

The Raman point map of the enamel-dentin junction (FIG. 5B) by the research grade Raman microscope (Xplora, Horiba Jobin Yvon, NJ) confirmed the expected stepwise transition of mineral content from low mineralization (dentin) to high mineralization (enamel). A similar transition in mineral content was also observed by the global Raman imaging set up (FIG. 5C); however, the information was limited to the center of the field of view.

Figure 8:
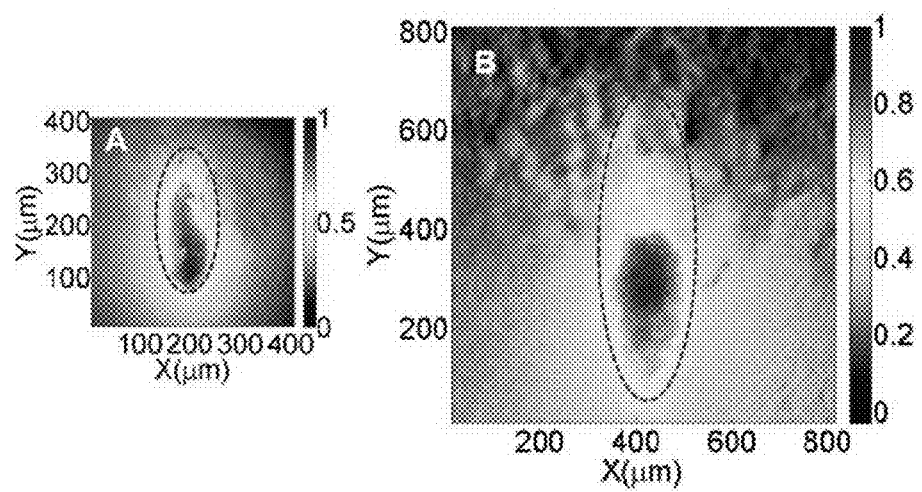
FIG. 8 illustrates wide-field Raman images (cylindrical lens engaged) using 25 mm lens (A) and 50 mm lens (B). The area of coverage (red dashed borders) was quadrupled by using lower magnification lenses. Other lenses can be used, including, but not limited to, concave and convex lenses, as well as other forms.

By using a cylindrical defocusing lens (~200 mm), the excitation profile was shaped as an elongated elliptical region to collect signal from an area of ~0.1×0.25 mm$^2$ (FIGS. 5C and 8A). The area coverage was quadrupled to ~0.2×0.5 mm$^2$ by using lower magnification lens (FIG. 8B).

The imaging data of the tooth demonstrated that 2-D Raman imaging can: 1) visualize mineral variations; 2) larger area of image can be obtained with lower magnification collection lens.

The insertion of microlens array into the system illustrated in FIG. 2 distributes the laser intensity of the field of view more effectively. Utilization of a high power laser and employment of image normalization routine, see FIG. 6, enables the system to image the entire field of view at faster acquisition times.

FIG. 7 illustrates another embodiment of a multi-lens array-containing Raman imaging system.

It is desirable that the system illustrated in FIG. 7 acquires Raman images over at least a 5×5 mm$^2$ area in a timeframe ranging from 0.1 to 10 seconds, depending on the Raman activity of the sample. The sub-units of the Raman imaging system include the excitation path, signal conditioning and acquisition, software interface and mechanical framework for sample positioning.

As described hereinabove, the multilens or microlens array discretizes the laser power to an array of spots which in turn spreads the laser power over the full field of view. This results in reduced risk of damage to the sample, while enabling the utilization of a high power laser. A high power laser can allow delivering 40-400 mW excitation laser light to each spot within the array image. Various available 2D CCD cameras based on silicon chips all have peeks sensitivity at green visible light range, which will provide greater signal collection than other wavelengths at a relatively low cost. Alternatively, other lasers can be utilized as described herein, such as a 1064 nm laser, which is suitable for investigators working on fluorescent specimens.

Beam Conditioning:

Beam shape is conditioned before being reflected on sample space in two regards: 1) expansion of beam to cover a larger field of view, and, 2) multifocal discretization of excitation. The laser beam is expanded to 6 mm for example by using a telescope lens pair. The expanded beam is delivered through a microlens array. Imaging area are expanded to the full range of the field of view of the imaging lens to reflect excitation arrays of 15×15 focused spots (FIG. 1). Each spot forms a new image at size comparable to that of the single image before inserting the microlens array (MLA). Expected performance in the spatial domain is listed in Table 1. The resolution was estimated using Abbe diffraction limit: D=0.61λ/NA, where d is the image diameter and NA is the numerical aperture of the objective lens.

The resulting beam is diverted to the sample by a dichroic mirror and focused on to the sample by objectives/lenses mounted on a rotating turret. Depending on the lens, the resulting illumination area can thus be tailored to cover regions as large as 5 mm×5 mm with spacing between each spot in illumination array from 5 μm to 250 μm (Table 1). Depending on the magnification of the lens, the spatial resolution will vary between 0.4 μm to 1.6 ppm. Depending on the application; the system can be configured at fixed magnification. Alternatively, by using a set of low to high magnification lenses, the system can also be configured as a multiscale imaging setup covering cm to micrometer size scales in one system when desired.

TABLE 1

| Lens | Field of View | Spatial Resolution | Image diameter w/o MLA | Image diameter with MLA | Image Spot Distance |
|---|---|---|---|---|---|
| 100X | 400 μm | 0.4 μm | 1 μm | 40 μm | 5 μm |
| 10X | 500 μm | 1.2 μm | 13 μm | 500 μm | 30 μm |
| 25 mm (1" aperture) | 1 μm | 0.7 μm | 33 μm | 1 μm | 100 μm |
| 100 mm (1" aperture) | 5 μm | 1.6 μm | 130 μm | 5 μm | 250 μm |

Signal Collection and Conditioning

Photons reflected from the samples are collected by the same lens, and pass through the dichroic mirror on the reflection path. An edge (or notch) filter is used to remove the Rayleigh line. Following this stage, the wavenumber (or wavenumber range) of interest is extracted.

In addition to a hyperspectral version of the system, the bandpass filter can, in one embodiment, offer imaging for a limited number of wavenumbers, for example up to about 500 wavenumbers utilizing a bandpass filter that is adjustable on a single axis and contain at least two different filters and for example from 2 to about 5 filters with.

Data Acquisition

The data can be acquired by an ultrasensitive 2D CCD camera, such as Andor Ikon-M 934, whose quantum efficiency is between 90-95% at 400-800 nm range. The camera also features negligible dark current with deep thermoelectric cooling as low as −100° C. This camera is equipped with high resolution sensors having 1024×1024 active pixels. The dark background, signal integration time, signal averaging and wavenumber scan range can automatically controlled by software, such as LabView software.

Data Processing

Since the Raman signal is proportional to the amount of excitation, variations in illumination over the space continuum need to be corrected. The variation of illumination over the sample stems from: 1) distortions/aberrations introduced by optical components, 2) surface curvature of the sample (when present) that introduces variations in depth of focus. These effects can be simply and expeditiously accounted for by acquisition of a reference image. Dividing the Raman image with the reference image normalizes for the relative variations in spatial intensity, which can be expressed as $$I_{corr} = \frac{I_{adjusted\ raw}}{I_{ref}},$$

where $I_{adjusted\ raw}$ is the intensity matrix of the raw image which can be adjusted by, for example, but not limited to smoothing, filtering or subjected to another form of numerical processing, $I_{ref}$ is intensity matrix of the reference image, while 6, is the intensity variance corrected final image.

Figure 6:
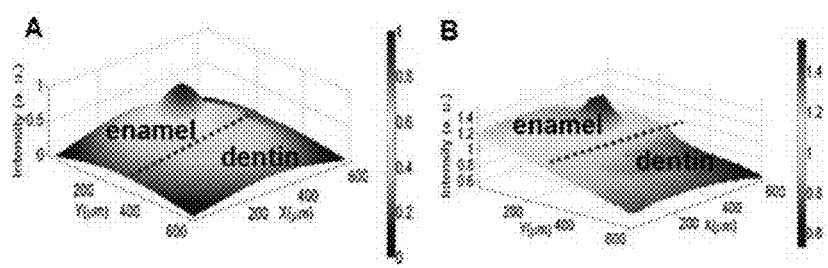
FIG. 6 illustrates A) global Raman image of an enamel-dentin junction B) Image in A was normalized by a reference image reflecting the intensity variations of excitation over the field of view. The normalization resulted in the recovery of information from a greater fraction of the field of view.

This reference image correction method is demonstrated in FIG. 6 by using the mineralization. In this case the mineral information is included at 960 cm$^{-1}$ whereas a second reading taken at 880 cm$^{-1}$ is used as the reference background. This reference image was used to divide the fluorescence background corrected image. FIG. 6A shows the image before normalization which is limited to less than 10% of the field of view. Following the normalization (FIG. 6B), the enamel/dentin contrast increased and information was recovered from more than 70% of the imaged area.

While in accordance with the patent statutes the best mode and preferred embodiment have been set forth, the scope of the invention is not limited thereto, but rather by the scope of the attached claims.

What is claimed is:

1. A Raman imaging system, comprising:
   an excitation source providing a beam; and
   a dual-axis controlled dielectric filter located downstream from the excitation source in a beam path that provides for hyperspectral selection, and
   a charge-coupled device located downstream from a lens array.

2. A Raman imaging system according to claim 1, wherein the dual-axis control dielectric filter includes a motorized wheel that can accommodate 1-10 band-pass filters which each have a different wave number.

3. The Raman imaging system according to claim 2, wherein the dual-axis control dielectric filter includes as azimuthal rotation that enables wavelength tuning to cover a wavelength range of ±250 cm$^{-1}$ about a central wave number.

4. The Raman imaging system according to claim 2, wherein a lens array is located downstream from the excitation source in the beam path and includes a plurality of lenses that split the beam into a plurality of beams, wherein the plurality of beams are adapted to be routed onto the sample.

5. The Raman imaging system according to claim 4, wherein the lens array is a microlens array, wherein a dichroic mirror is located downstream from the microlens array and able to route the plurality of beams through a focusing lens that is adapted to focus the plurality of beams onto the sample, wherein the resulting Raman signal is reroutable through the dichroic mirror.

6. The Raman imaging system according to claim 5, wherein the excitation source is a monochromatic laser having a wavelength from about 250 to 1064 nm.

7. The Raman imaging system according to claim 6, wherein a flip beam splitter is present downstream from the dual-axis control dielectric filter and can be switched to route the Raman signal to either the charge-coupled device or a spectrometer located downstream from the flip beam splitter.

8. The Raman imaging system according to claim 7, wherein the lens array increases a cross sectional area of the beam to an area that is at least 25% larger than an area of the beam incident on a first lens of the plurality of lenses.

9. The Raman imaging system according to claim 8, wherein the area increase is at least 50%.

10. A Raman imaging system, comprising:
    an excitation source providing a beam; and
    a dual-axis controlled dielectric filter located downstream from the excitation source in a beam path that provides for hyperspectral selection, and
    a charge-coupled device located downstream from a lens array, wherein the dual-axis control dielectric filter includes a motorized wheel that can accommodate 1-10 band-pass filters which each have a different wave number, wherein the dual-axis control dielectric filter includes as azimuthal rotation that enables wavelength tuning to cover a wavelength range of ±250 cm$^{-1}$ about a central wave number.

11. The Raman imaging system according to claim 10, wherein a lens array is located downstream from the excitation source in the beam path and includes a plurality of lenses that split the beam into a plurality of beams, wherein the plurality of beams are adapted to be routed onto the sample.

12. The Raman imaging system according to claim 11, wherein the lens array is a microlens array, wherein a dichroic mirror is located downstream from the microlens array and able to route the plurality of beams through a focusing lens that is adapted to focus the plurality of beams onto the sample, wherein the resulting Raman signal is reroutable through the dichroic mirror.

13. The Raman imaging system according to claim 12, wherein the excitation source is a monochromatic laser having a wavelength from about 250 to 1064 nm.

14. The Raman imaging system according to claim 13, wherein a flip beam splitter is present downstream from the dual-axis control dielectric filter and can be switched to route the Raman signal to either the charge-coupled device or a spectrometer located downstream from the flip beam splitter.

15. The Raman imaging system according to claim 14, wherein the lens array increases a cross sectional area of the beam to an area that is at least 25% larger than an area of the beam incident on a first lens of the plurality of lenses.

* * * * *

UNITED STATES PATENT AND TRADEMARK OFFICE
CERTIFICATE OF CORRECTION

| | | |
|---|---|---|
| PATENT NO. | : 10,024,798 B2 | Page 1 of 1 |
| APPLICATION NO. | : 14/600603 | |
| DATED | : July 17, 2018 | |
| INVENTOR(S) | : Ozan Akkus et al. | |

It is certified that error appears in the above-identified patent and that said Letters Patent is hereby corrected as shown below:

In the Specification

In Column 1, after the title please list the following:
-- GOVERNMENT LICENSE RIGHTS
This invention was made with government support under Grant No. DMR-1531035 awarded by the National Science Foundation. The United States government has certain rights in the invention. --

Signed and Sealed this
Sixth Day of November, 2018

Andrei Iancu
*Director of the United States Patent and Trademark Office*